United States Patent [19]

Katayama et al.

[11] Patent Number: 4,672,560

[45] Date of Patent: Jun. 9, 1987

[54] ENTHALPY CALCULATOR

[75] Inventors: Akifumi Katayama, Fujisawa; Keijirou Mori, Kanagawa; Satoshi Ueda, Kamakura, all of Japan

[73] Assignee: Matsushita Electric Industrial Co., Ltd., Kadoma, Japan

[21] Appl. No.: 843,859

[22] PCT Filed: Jan. 10, 1983

[86] PCT No.: PCT/JP83/00005

§ 371 Date: Aug. 26, 1983

§ 102(e) Date: Aug. 26, 1983

Related U.S. Application Data

[63] Continuation-in-part of Ser. No. 532,023, Aug. 26, 1983, abandoned.

[30] Foreign Application Priority Data

Jan. 11, 1982 [JP] Japan .................................. 57-2453

[51] Int. Cl.[4] .......................................... G01K 17/00
[52] U.S. Cl. ..................... 364/556; 73/336; 364/557
[58] Field of Search ................ 364/556, 557; 73/336; 374/31, 35, 170; 236/44 R, 44 C

[56] References Cited

U.S. PATENT DOCUMENTS

| | | | |
|---|---|---|---|
| 3,866,026 | 2/1975 | de Vivy | 364/556 |
| 3,946,308 | 3/1976 | Miura et al. | 73/336 |
| 4,078,431 | 3/1978 | Mott | 73/336 |
| 4,182,180 | 1/1980 | Mott | 73/336 |
| 4,380,155 | 4/1983 | Paddock et al. | 364/557 |
| 4,574,626 | 3/1986 | Kaya et al. | 364/557 |

FOREIGN PATENT DOCUMENTS

| | | | |
|---|---|---|---|
| 0157677 | 12/1979 | Japan | 73/336 |
| 58-120157 | 7/1983 | Japan | 364/556 |
| 0075143 | 4/1984 | Japan | 73/336 |

Primary Examiner—Parshotam S. Lall
Attorney, Agent, or Firm—Wenderoth, Lind & Ponack

[57] ABSTRACT

An enthalpy calculator outputs a value of enthalpy directly calculated from two measured items such as dry bulb temperature and relative humidity, and includes: a humidity sensor for converting relative humidity into an electrical signal; a temperature sensor for converting dry bulb temperature into an electrical signal; and arithmetic units for outputting the calculated enthalpy value as an electrical signal after performing a calculation based on the signals input by the temperature sensor 12 and the humidity sensor 5 in accordance with the following equation:

$$i = at\psi + bt + c\psi + d$$

wherein
a, b, c, and d are preselected constants, and:
t: dry bulb temperature (°C.)
$\psi$: relative humidity (%), a, b, c, and d being selected so that $|i - i_0| \leq 0.5$ within a fixed temperature range if:

$$i_0 = 0.240t + (597.3 + 0.441t)x$$

and $$x = 0.622 \cdot \psi \cdot h / P - \psi \cdot h$$

wherein
P: atmospheric pressure (mmHg) around the output unit
h: saturated vapor pressure (mmHg) under atmospheric pressure P.

4 Claims, 14 Drawing Figures

ENTHALPY CALCULATOR

This application is a continuation-in-part of application Ser. No. 532,023, filed Aug. 26, 1983, now abandoned.

BACKGROUND OF THE INVENTION

This invention relates to an enthalpy calculator in which the enthalpy of a body of gas or humid air is calculated by an arithmetic unit in accordance with an enthalpy equation from the measured temperature and relative humidity of the body of gas, and in which the calculated value is converted into electrical signals which are output therefrom.

The enthalpy of humid air is obtained by the following equations (A) and (B) when the temperature and pressure thereof are within the ranges in which everyday air conditioning is carried out.

$$i = 0.240t + (597.3 + 0.441t)x \tag{A}$$

$$x = 0.622 h_s \cdot \psi / P - h_s \cdot \psi \tag{B}$$

where
- t: dry bulb temperature (°C),
- x: humidity ratio (kg/kg'),
- P: atmospheric pressure (mmHg),
- $h_s$: saturated vapor pressure (mmHg) at temperature t,
- $\psi$: relative humidity (%),
- i: enthalpy (Kcal/kg').

With equation (B), a complicated calculation is needed in which a value obtained by an approximate expression that has hitherto been disclosed, such as the IFC Formulation for Industrial Use, must be substituted therein to obtain the saturated vapor pressure.

Accordingly, to obtain a value for the enthalpy of humid air using a conventional arithmetic unit it has been necessary to find the value of one other factor, in addition to the dry bulb temperature, as a measured value. That is to say, conventional methods depend on the humidity ratio, wet bulb temperature, relative humidity, and dew point temperature and, whichever method is used, the values measured are converted into enthalpy in accordance with equations (A) and (B) using an electronic computer. Any method depending on finding the dew point temperature or the humidity ratio has the drawbacks of the slow reaction speed and expensive sensing elements, and other methods depending on the wet bulb temperature, relative humidity, and dew point temperature have a disadvantage in that the solving of complicated equations are required.

SUMMARY OF THE INVENTION

According to this invention, the value of enthalpy is given by an arithmetic unit performing calculations using the following enthalpy calculation equations (C) and (D), which consist of a sum of the product of a linear function of the dry bulb temperature multiplied by a linear function of the relative humidity, and constants, the dry bulb temperature and the relative humidity being important elements in the air-conditioning of the environment, when a limitation is imposed on the range of temperature (about 20°–30° C.) of air in a room when healthy air conditioning is provided.

$$i = a \cdot t \cdot \psi + b \cdot t + c \cdot \psi + d \tag{C}$$

$$i = a(t + P) \cdot (\psi + q) + r \tag{D}$$

where a, b, c, d, P, q, and r are all constants.

By using equations (C) and (D) according to this invention, a value of enthalpy which is more accurate than that read from a physchrometric diagram can be found easily without performing the conventional complicated calculations based on equations (A) and (B), provided that the temperature at which the enthalpy is calculated is within the temperature range used in practice.

Figure 1:
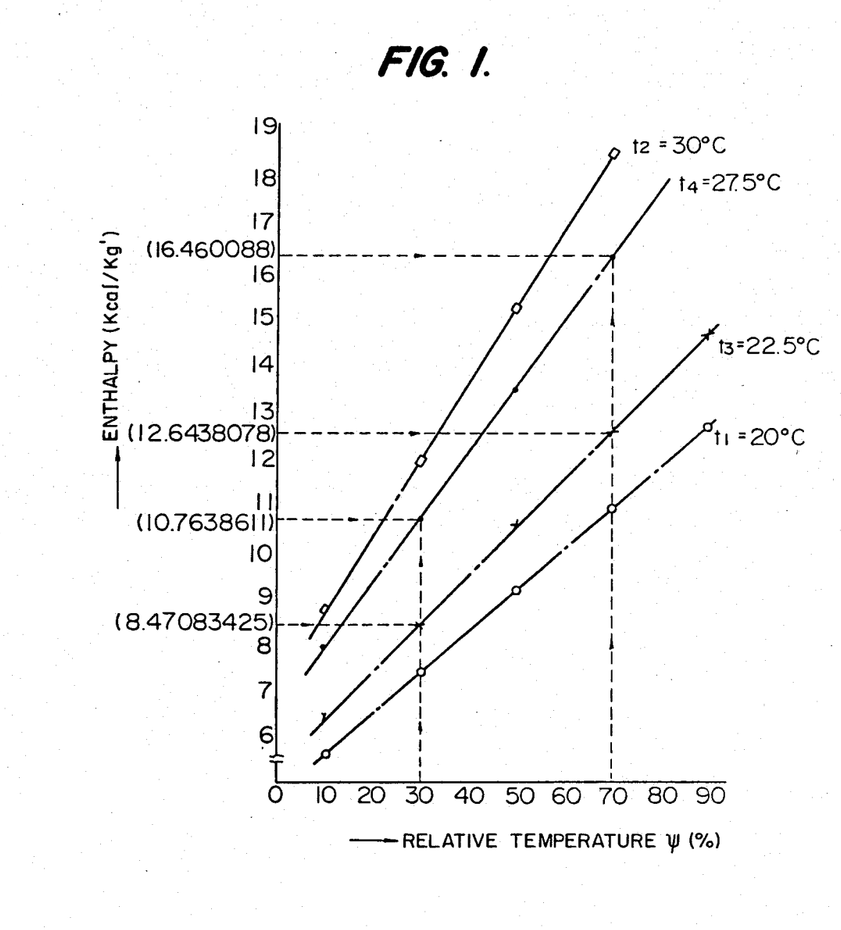
FIG. 1 is a graph of the relationship between relative humidity and enthalpy.

The method of deriving equations (C) or (D) will now be described. FIG. 1 is a graph showing the values of enthalpy i calculated from a psychrometric diagram (i−x diagram) and the fundamental equations (A) and (B) for calculating enthalpy, with the condition that the dry bulb temperature is kept constant. In this case, the enthalpy can be approximated by a linear function of the relative humidity as expressed by equation (E) as follows:

$$i = m\psi + n \tag{E}$$

where m and n are constants. If corrections to m and n at each degree of temperature are examined, they can be expressed by approximate expressions (F) and (G) which are linear functions of the temperature t within a certain range temperature of $t_1$ to $t_2$, as follows:

$$m = at + c \tag{F}$$

$$n = bt + d \tag{G}$$

where a, b, c, and d are constants.

Therefore, by substituting equations (F) and (G) into equation (E), equations (C) and (D) can be obtained.

According to this invention, by measuring the dry bulb temperature and the relative humidity, it is possible, within a certain range of temperatures, to reduce the difference between the enthalpy value obtained by the simple calculation expressed by equation (C) or (D) and that obtained by the fundamental equations (A) and (B) to a minimum.

The following equation (H) provides values of the coefficients a, b, c, and d applied to the range of temperature from 20° to 30° C. using equation (C), based on temperatures set at 22.5° and 27.5° C. and relative humidities at 30 and 70%.

$$i = 7.616 \times 10^{-3} \psi \cdot t + 0.2301 t - 0.06704 \psi + 0.1634 \tag{H}$$

TABLE 1

| Relative humidity (%) | (kcal/kg') $i - i_0$ Temperature (°C.) | | | | | |
|---|---|---|---|---|---|---|
| | 20 | 22 | 24 | 26 | 28 | 30 |
| 10 | −0.053 | −0.036 | −0.033 | −0.044 | −0.071 | −0.116 |
| 20 | −0.076 | −0.024 | 0.002 | −0.002 | −0.039 | −0.111 |
| 30 | −0.102 | −0.016 | 0.030 | 0.031 | −0.018 | −0.120 |
| 40 | −0.133 | −0.014 | 0.051 | 0.055 | −0.007 | −0.143 |
| 50 | −0.168 | −0.017 | 0.066 | 0.071 | −0.008 | −0.180 |
| 60 | −0.208 | −0.025 | 0.073 | 0.078 | −0.020 | −0.231 |
| 70 | −0.251 | −0.039 | 0.074 | 0.076 | −0.043 | −0.297 |
| 80 | −0.298 | −0.058 | 0.068 | 0.066 | −0.077 | −0.377 |
| 90 | −0.350 | −0.082 | 0.054 | 0.046 | −0.12 | −0.422 |

In this case, using FIG. 1, the linear equations when $t_3 = 22.5°$ C. and $t_4 = 27.5°$ C., respectively, are:

$$i = (0.104324338)\psi + 5.3411041 \text{ (at } t_3)$$

$$i = (0.142405671)\psi + 6.49169099 \text{ (at } t_4)$$

Figure 2:
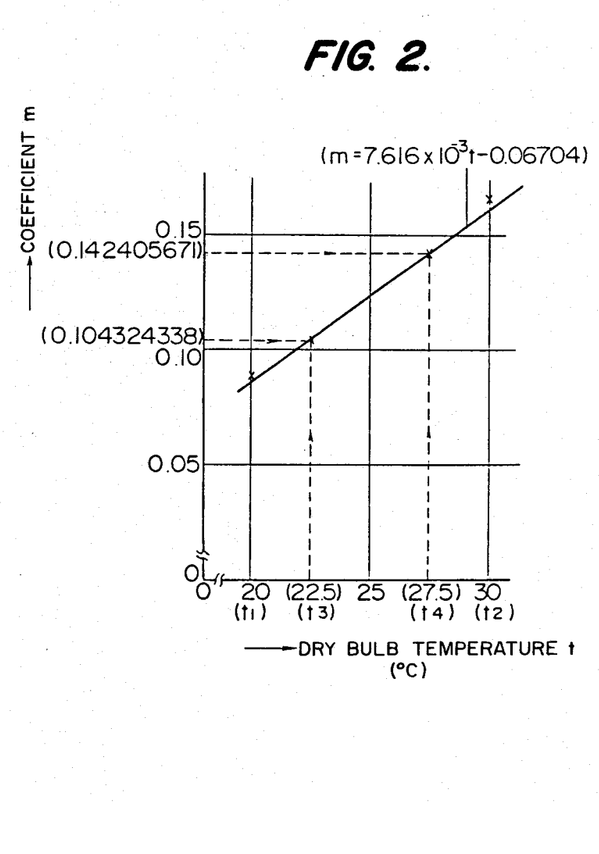
FIG. 2 is a graph of the relationship between dry bulb temperature and the coefficient m.
Figure 3:
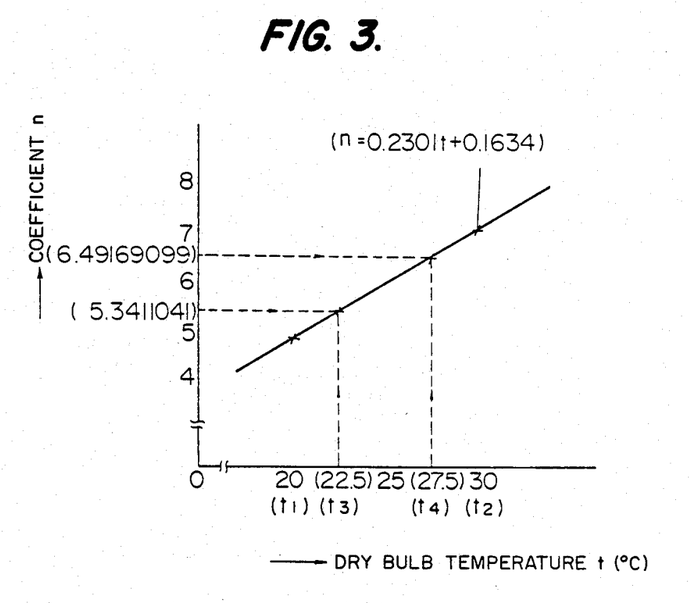
FIG. 3 is a graph of the relationship between dry bulb temperature and the coefficient n.

Within the temperature range of $t_3$ to $t_4$ these values can be shown graphically as in FIGS. 2 and 3, to provide:

$$m = 7.616 \times 10^{-3} t - 0.06704$$

$$n = 0.2301 t + 0.1634.$$

Hence, the constants a through d are:
a = 7.616 × 10$^{-3}$
b = 0.2301
c = −0.06704
d = 0.1634

As shown in Table 1, the value of enthalpy i obtained from equation (H) is so accurate that the difference between it and that obtained from the fundamental equations (A) and (B) is at most 0.5 within the whole of the temperature range of 20° to 30° C., this is sufficiently accurate for application within the range of temperatures and relative humidities used in practice. The temperature range on which the calculation is performed can easily be changed by finding values for the constants in equations (C) and (D) afer changing the temperature range.

An arithmetic unit for performing the calculations based on equation (D) modified from equation (C) is composed of a multiplier for multiplying the linear function of temperature with that of relative humidity, both of which having been converted into electrical signals, and of an adder for summing the constants, so that a handy enthalpy calculation device which outputs an electrical signal representing the enthalpy i can be obtained.

DESCRIPTION OF THE PREFERRED EMBODIMENT

A description will now be made of an embodiment of an enthalpy computation unit performing calculations using equation (D), with reference to FIGS. 4 through 9.

Figure 4:
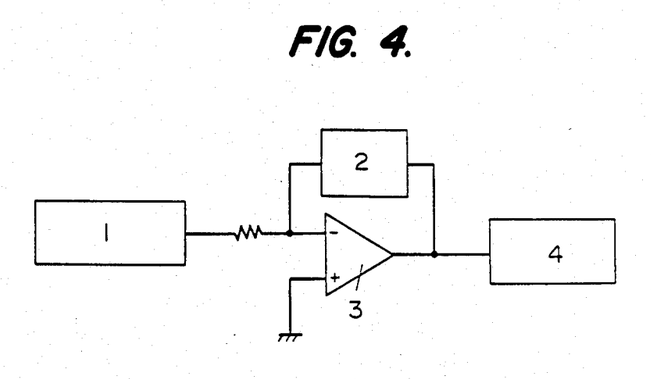
FIG. 4 is a block diagram of the composition of an embodiment of this invention.

FIG. 4 is a diagram of the basic composition of an arithmetic unit as an embodiment of this invention, wherein reference numeral 1 denotes a humidity signal output section for outputting an voltage expressed by a linear function whose variable is the relative humidity; numeral 2 denotes a temperature signal output section which changes the amplitude thereof in response to a resistance expressed by a linear function whosee variable is the temperature; and numeral 3 denotes a multiplier which multiplies the temperature output signal by the relative humidity output signal and outputs a value of enthalpy as a voltage which is fed to an output section 4.

Figure 5:
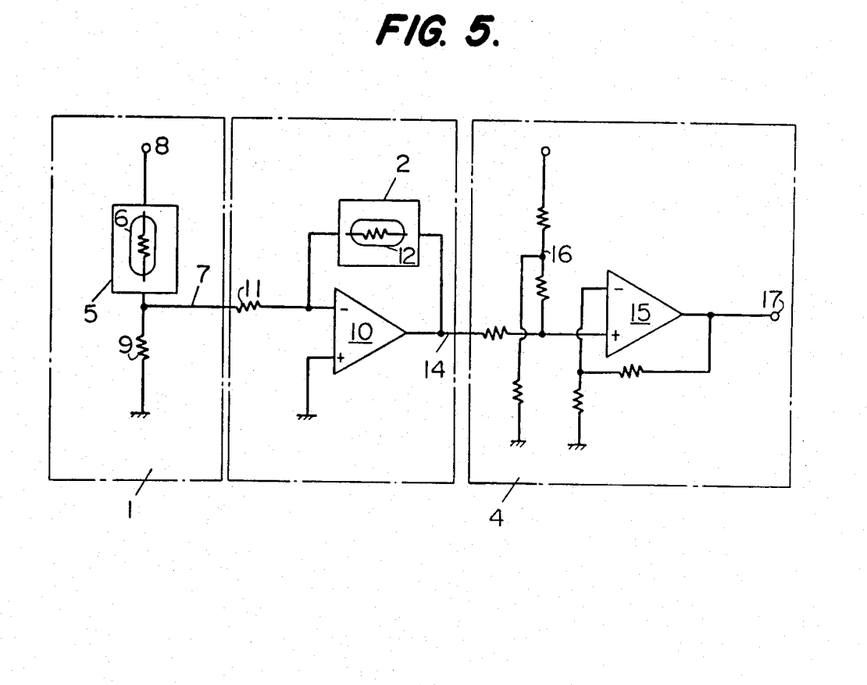
FIG. 5 is a circuit diagram of an output unit in accordance with the present invention.

In FIG. 5, numeral 5 indicates a humidity sensor which comprises a resistor 6 for sensing variations in humidity as variations in its electrical resistance. The voltage at a terminal 7 is a value obtained by dividing a voltage applied to a terminal 8 by the ratio of the resistances of humidity sensors 5 and 9, so that a linear function of the measured relative humidity is established. This comprises the humidity signal output section 1. Numeral 10 denotes an operational amplifier in which, when a voltage expressed as a linear function of relative humidity is input to an inverting input terminal thereof, a voltage is output from a terminal 14 in response to the amplification determined by the combined resistance of a resistor 11 and a thermistor 12. The thermistor 12 is a temperature sensor with a large B constant, and makes up the temperature signal output section 2 expressed by the linear function whose variable is temperature. The voltage output from the terminal 14 is a product of the linear function whose variable is relative humidity multiplied by the other linear function whose variable is temperature. The output section 4 is a summation section for summing the constants of the approximate expression (D) and for adding the voltages at terminals 14 and 16 by using an operational amplifier 15 as an adder. As a result, a value of the enthalpy expressed by the approximate expression (D) is output from a terminal 17 as a voltage.

Figure 6:
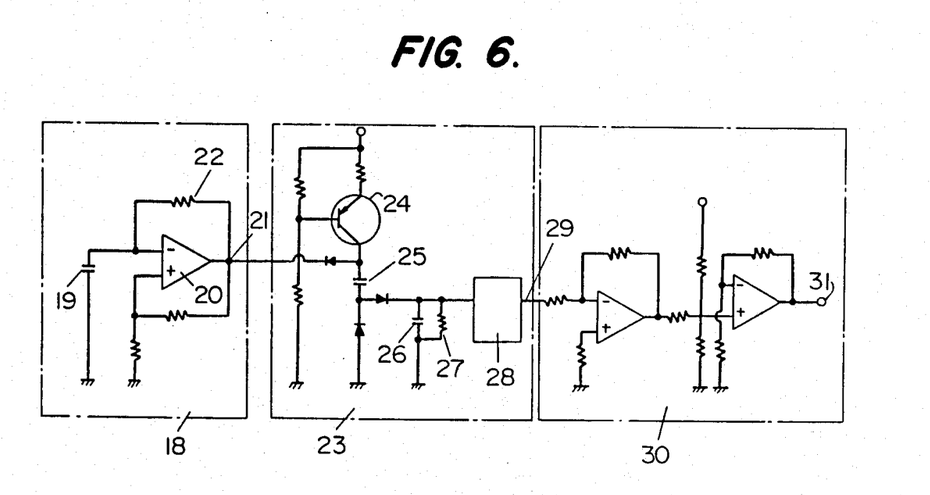
FIG. 6 is a circuit diagram of another example of an output unit in accordance with the present invention.

FIG. 6 shows another example of a humidity signal output section in accordance with the present invention. Numeral 18 indicates an oscillation circuit, in which, by connecting a capacitor 19 for sensing humidity variations as variations in its electrostatic capacity to the input side of an inverting input terminal of an operational amplifier 20, a frequency which is inversely proportional to the capacity of the capacitor 19 and that of a resistor 22 is generated from an output terminal 21 of the operational amplifier 20. Numeral 23 represents a frequency-voltage conversion section in which a collector current at a certain voltage is passed through a transistor 24 only when the potential at terminal 21 is high, so as to charge and smooth the voltage of capacitors 25 and 26, and, at the same time, the charge on the capacitors is discharged by a resistor 27 connected parallel to the capacitor 26 so that the potential at capacitor 26 is proportional to the frequency. Furthermore, a voltage which has been smoothed by passing it through a filter 28 is output from a terminal 29. Numeral 30 indicates a correction section for correcting the voltage output from the frequency-voltage conversion section 23, so as to output the voltage required for the calculation from a terminal 31.

Figure 7:
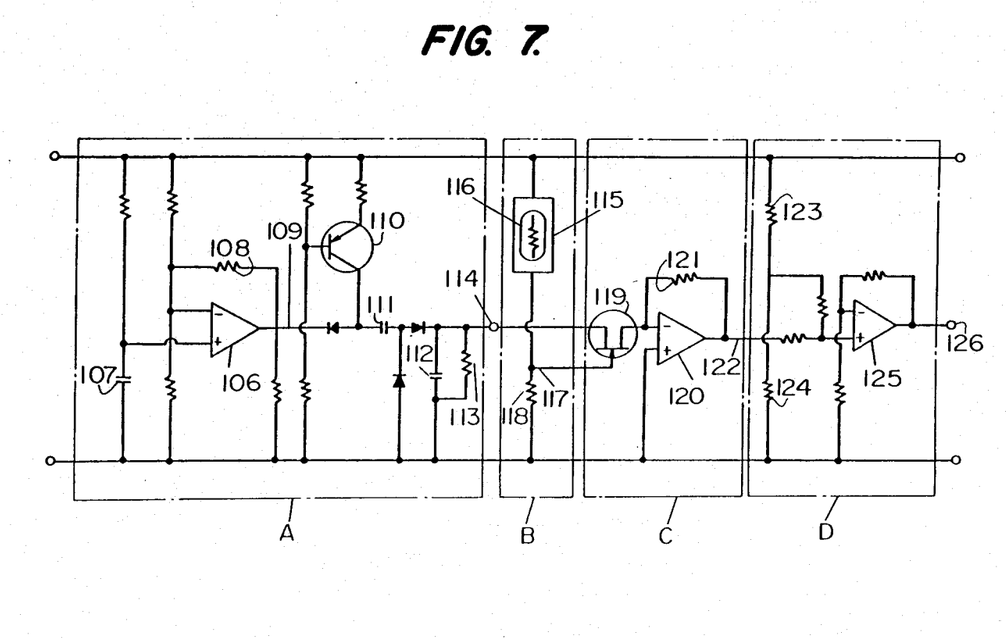
FIGS. 7, 8, and 9 are circuit diagrams of other embodiments of this invention.

FIG. 7 shows another embodiment of this invention in which reference character A denotes a relative humidity signal output section which outputs a constant rectangular-wave whose frequency is inversely proportional to the capacity of a capacitor 107 and the value of a resistor 108 from an output terminal 109 of an operational amplifier 106 when the capacitor 107 is connected to a non-inverting input of the operational amplifier 106, and when the resistor 108 is connected by a negative feedback circuit. When the potential at terminal 109 is high, a collector current at a certain voltage flows through a transistor 110 to charge a capacitor 111 which senses humidity variations as variations in its electrostatic capacity as well as charging and smoothing a voltage of a capacitor 112. The discharge of the stored charge is performed by a resistor 113 to the capacitor 112 and, as a result, the potential at a terminal 114 is proportional to the capacity of the capacitor 111. In other words, the potential at terminal 114 is expressed by a linear function whose variable is relative humidity.

Reference character B indicates a temperature signal output section in which a combined resistance 115 consists of the resistance of a resistor 116 sensing temperature variations as variations in resistance, and the potential at a terminal 117 corresponds to a dividend obtained by dividing the voltage of the power source by the ratio of the combined resistance 115 to the resistance of the resistor 118. That is, the potential at terminal 117 can be expressed approximately as a linear function of the resistance 116, i.e., it varies with temperature.

Character C denotes a multiplication section comprising a FET 119 and an operational amplifier 120, which multiplies the input voltages at the terminals 114 and 117 and outputs from a terminal 112a voltage amplified according to the amplification determined by a resistance 121 and FET 119.

Character D indicates an addition section composed of an operational amplifier 125 used as an adder for adding the voltage at terminal 122 to a voltage obtained by dividing the voltage of the power source by the ratio of resistance between resistors 123 and 124, and for outputting the calculated enthalpy as a voltage from terminal 126.

Figure 8:
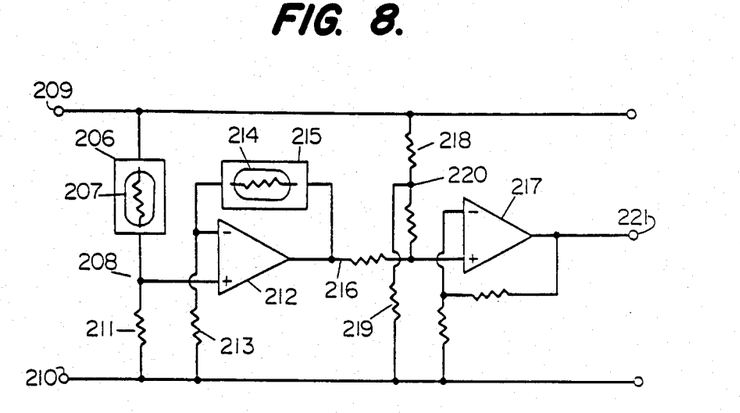

FIG. 8 shows another embodiment of the present invention in which numeral 206 denotes a combined resistance composed of a resistor 207 for sensing temperature variations converted into voltage variations. The voltage at a terminal 208 is a value obtained by dividing the voltage between terminals 209 and 210 by the ratio of resistance 206 and 211, and can be expressed in terms of a linear function of the resistance of resistor 207, i.e., temperature. An operational amplifier 212 is an in-phase amplifier in which, when the voltage expressed by the linear function of temperature is input to the non-inverting input terminal thereof, a voltage in response to the amplification determined by a combined resistance 215 comprising the resistance of a resistor 213, and that of an other resistor 214 which senses relative humidity variations as resistance variations, is output from a terminal 216. Assuming that the value of the combined resistance 215 is a resistance expressed by a linear function of relative humidity, the voltage at terminal 216 is that obtained by the multiplication of the linear function of temperature with that of relative humidity. An operational amplifier 217 is an in-phase adder which outputs a voltage from a terminal 221 after adding the voltage at terminal 216 to that at a terminal 220 which has a potential obtained by dividing the voltage between terminals 209 and 210 by the ratio of resistances of resistors 218 and 219. The voltage at a terminal 221 corresponds to the calculated enthalpy expressed by the sum of the product of the linear functions of temperature and relative humidity, and constants.

Figure 9:
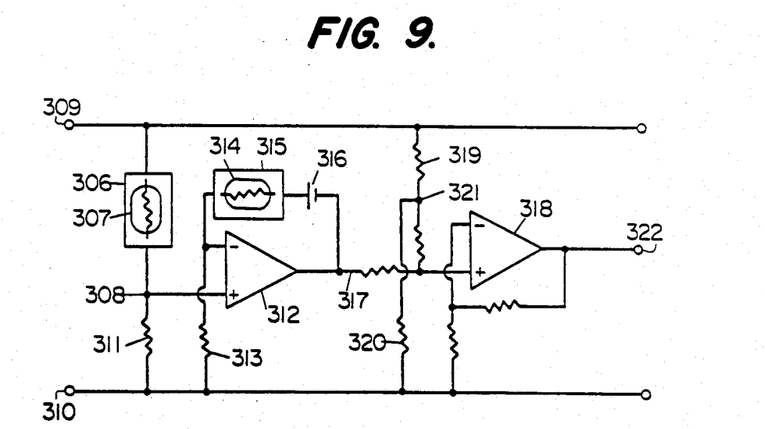

FIG. 9 shows still another embodiment of this invention, wherein numeral 306 represents a combined resistance comprising a resistor 307 sensing relative humidity variations as resistance variations. The voltage at a terminal 308 corresponds to a value obtained by dividing the voltage between resistors 306 and 311, and can be expressed by the resistance of resistor 307, i.e., a linear function whose variable is relative humidity. An operational amplifier 312 is an in-phase amplifier in which, when the voltage indicating the linear function is input to a non-inverting input terminal thereof, a voltage corresponding to the amplification determined by a combined resistance 315 comprising the resistance of a resistor 313 and that of a resistor 314 which senses temperature variations as resistance variations, and by a constant voltage output section 316, is output from a terminal 317.

Although it is possible to transform the value of the combined resistance 315 into a resistance that can be expressed by the resistor 314, i.e., a linear function of temperature, it is difficult to make the constant terms agree with the values in equation (D) but, by providing a constant voltage output section parallel to the resistor 315, agreement of the constant terms with their computed values is made easier. Therefore, the voltage at terminal 317 can be expressed as a product of the linear functions of temperature and relative humidity. An operational amplifier 318 is an in-phase adder for adding the voltages at terminal 317 to that at a terminal 321 which has a potential obtained by dividing the voltage between terminals 309 and 310 by the resistance ratio of resistors 319 and 320, and it outputs the calculated voltage from a terminal 322. That is to say, the voltage at terminal 322 corresponds to an enthalpy value expressed as a sum of the product of the linear functions of temperature and relative humidity, and a constant term.

Figure 10:
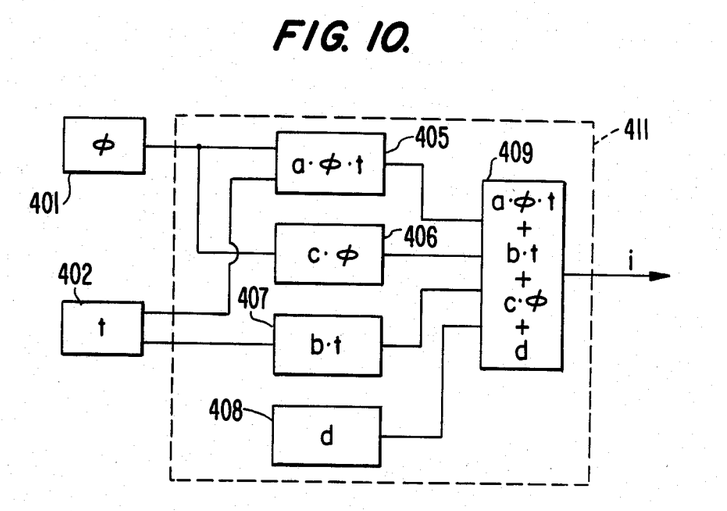
FIG. 10 is a basic configuration of another embodiment of the present invention.

FIG. 10 is a basic configuration of an embodiment according to an arithmetic formula (D), $i=a(t+p)(\psi+q)+r$, of the present invention, wherein element 401 denotes a humidity signal element which delivers a humidity signal proportional to the relative humidity of a gas; element 402 is a temperature signal element which delivers a temperature signal proportional to the humidity of said gas; element 405 is a temperature-humidity multiplying means which multiplies the temperature signal, humidity signal and constant a, and delivers a signal proportional to the product; element 406 is a humidity multiplying means which delivers the product signal of the humidity signal value and constant C; element 407 is a temperature multiplying means which delivers the product signal of the temperature signal value and constant b; element 408 is a constant setting means which delivers a signal corresponding to constant d; element 409 is an adding means which adds up the outputs from said temperature-humidity multiplying means, humidity multiplying means, temperature multiplying means, and constant setting means, and delivers a signal corresponding to the enthalpy value, and element 411 is an enthalpy calculating element which is composed of temperature-humidity multiplying means, temperature multiplying means, humidity multiplying means and constant setting means, and receives the temperature signal and the humidity signal, and delivers a signal corresponding to the enthalpy value shown in formula (D).

Figure 11:
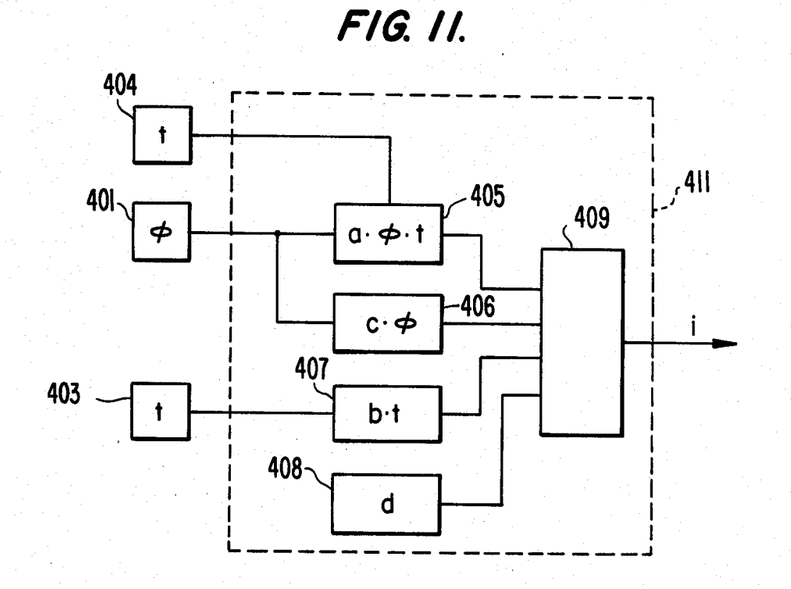
FIG. 11 illustrates the temperature signal element 402 of FIG. 10.

In FIG. 11, the temperature signal element 402 in FIG. 10 is divided into a first temperature signal element 403 and a second temperature signal element 404. The purpose of this division is to form the temperature-humidity multiplying means of a simple electronic circuit so as to easily obtain the product of the temperature signal, the humidity signal, and the constant a.

Figure 12:
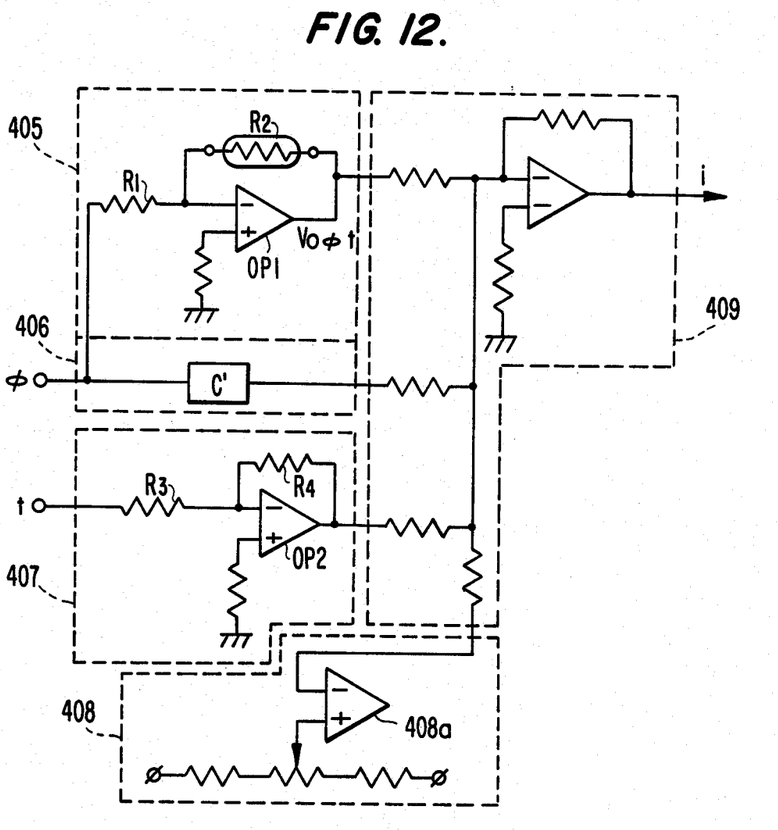
FIG. 12 is a practical example of the basic configuration shown in FIG. 11.

FIG. 12 is a practical example of the basic configuration shown in FIG. 11, wherein the temperature-humidity multiplying means 405 is a well-known inverting amplifier, being composed of input resistance R1, feedback resistance R2, and operational amplifier OP1. The relationship between its output $V_{0\psi t}$ and input $\phi$ is expressed as $v_{0\psi t} = R_2/R_1 \psi$. When a temperature sensing resistor element whose temperature coefficient is $\alpha$ and whose resistance at reference temperature is $R_0$ is used as the feedback resistance $R_2$, since $R_2 = R_0(1+\alpha t)$, the output $v_{0\psi t}$ of the temperature-humidity multiplying means 405 is $$v_{0\phi t} = \left( \frac{R_0}{R_1} + \frac{\alpha R_0}{R_1} t \right) \times \psi \quad (1)$$

$$= \frac{\alpha R_0}{R_1} t \cdot \psi + \frac{R_0}{R_1} \cdot \psi$$

where the first term $\alpha R_0/R$ is the constant a in formula (D), and the second term is a term proportional to the humidity value which has occurred subordinately. As a result of generation of this term, the constant c of the humidity multiplying means becomes different from the constant c in formula (D). This corrective formula is $c' = c - R_0/R_1$. Here, by selecting the constant of the humidity multiplying means 406 as $c'$, the output $v_{0\psi t}$ of the humidity multiplying means 406 corresponding to humidity signal $\psi$ is $$v_{0\phi t} = c' \cdot \psi = (c - R_0/R_1) \cdot \psi \quad (2)$$

$$= c \cdot \psi - (R_0/R_1) \cdot \psi$$

The second terms of eqs. (1) and (2), which differs only in the signs, are mutually canceled at the time of addition to determine formula (D), and only the first terms of these two equations are left over and added up. Constant $c'$ is set in the degree of amplification of the amplifier (not shown) which constitutes the humidity product signal element 406. On the other hand, the temperature multiplying means 407 is an amplifier circuit composed of operational amplifier OP2, input resistance R3 and feedback resistance R4, and the relationship of its output $v_{0t}$ and input $v_t$ is expressed as $v_{0t} = R_4/R_3 \cdot t$. Therefore, the constant b can be set in the relationship of $b = R_4/R_3$. The constant setting means 408 is composed of the output part of the signal voltage corresponding to the constant D, dividing the reference voltage by the resistance, and the impedance converting part 408a to convert the output impedance of its signal into a low impedance.

Finally, in the adding means 409, the signal outputs from said temperature-humidity multiplying means, humidity multiplying means, temperature multiplying means, and constant setting means are added up, and an output signal corresponding to the enthalpy value shown in formula (D) is synthesized and delivered.

In the calculation of enthalpy value according to formula (D), it is required that the temperature signal t and humidity signal $\psi$ be proportional to the temperature and humidity to be measured, respectively. Generating devices of humidity signal and temperature signal are shown in FIG. 13 and FIG. 14.

Figure 13:
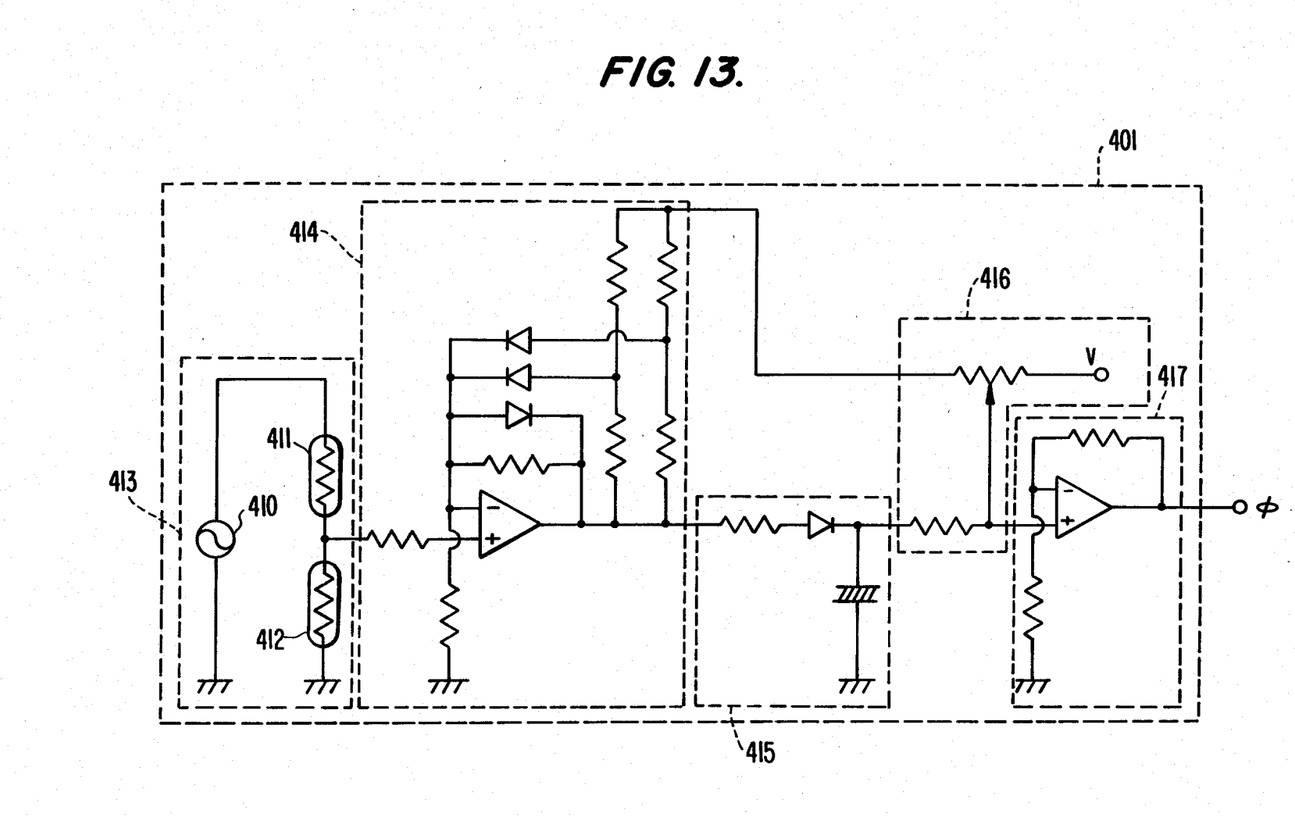
FIG. 13 shows a configuration of the humidity signal element 401 illustrated in FIG. 11.

FIG. 13 shows a configuration of the humidity signal element 401, comprising a humidity detector 413, and a polygonal line approximating element 414, and a rectifying and smoothing element 415, and a bias adjusting element 416, and an amplifier 417. The humidity detector 413 is a series circuit consisting of alternating-current power source 410, and a humidity sensing resistor element 411, and a temperature sensing resistor element 412, and the voltage across the temperature sensing resistor element 412 is picked up as a humidity signal. This temperature sensing resistor element is intended to compensate for the temperature characteristics of the humidity sensing resistor element. Incidentally, it is derived from the characteristics of the humidity sensing resistor element that a humidity signal is taken from the temperature sensing resistor element which is connected in series to the humidity sensing resistor element 411. Because of the characteristics of the element, when the relative humidity of the atmosphere rises, the resistance of the element decreases. On the other hand, the necessary humidity signal is proportional to the relative humidity. A voltage of a required direction can be obtained from the terminal voltage of the temperature sensing resistor element 412 connected in series to the humidity sensing resistor element 411. The humidity signal detected by the humidity detector 413 is applied into the polygonal line approximating element 414, where the relative humidity and relative humidity signal are corrected into a linear function. The output of this polygonal line approximating element 414 is an alternating-current signal, which is converted into a direct-current signal in the next stage of the rectifying and smoothing element 415. The bias adjusting element 416 is the zero point adjusting element of the humidity signal from the rectifying and smoothing element 415, and as a result of this adjustment, the humidity signal shows a value proportional to the ambient relative humidity of the humidity sensing resistor element 411.

Figure 14:
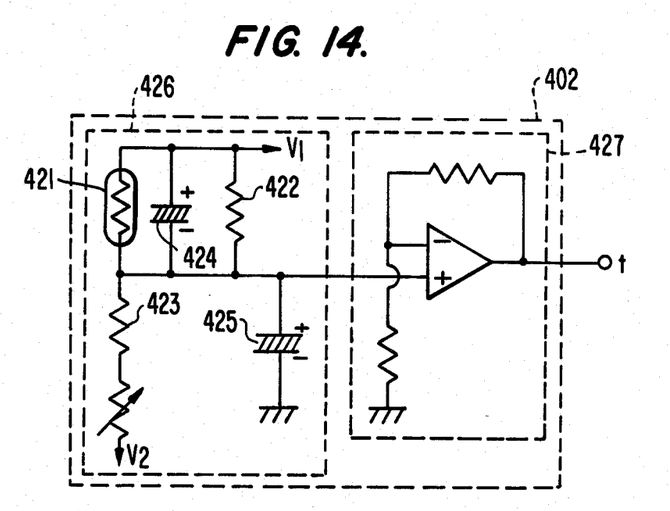
FIG. 14 illustrates the configuration of the temperature signal element 402 of FIG. 11.

A practical example of the configuration of the temperature signal element 402, is shown in FIG. 14. The temperature signal element 402 consists of temperature detector 426 and amplifier 427, and it detects the ambient temperature, and delivers a temperature signal proportional to it. The temperature detector 426 is composed of temperature sensing resistor element 421, and a parallel resistance 422, and a series resistance 423, and noise suppressing capacitors 424 and 425, and power supplies $V_1$ and $V_2$. As the temperature sensing resistor element 421 responds to the ambient temperature, its resistance varies, and a temperature signal proportional to the ambient temperature is delivered. This temperature signal is amplified in the amplifier 427, and a necessary temperature signal is obtained.

As has been described, an enthalpy output unit according to this invention uses a simple equation expressed as a sum of linear functions of relative humidity and temperature, and a term of summed constants; is capable of outputting a very accurate enthalpy value induced directly and easily from two measured items such as temperature and relative humidity; enables the construction of a circuit with only a few components; and enables a shift in the temperature range by an alteration of the constants in the circuit, so that it can be utilized over a wide range. The measured items required for the calculation are the dry bulb temperature and the relative humidity which are the most important factors for an index of environmental conditions and, accordingly, many advantages including the possibility of the direct application thereof to air conditioning control is provided thereby.

What is claimed is:

1. An enthalpy output device comprising: a humidity sensor for converting a relative humidity into an electrical signal; a temperature sensor for converting dry bulb temperature into an electrical signal; a first multiplying means for multiplying said electrical signal of said humidity sensor by a first specified voltage; a second multiplying means for multiplying said electrical signal of said temperature sensor by a second specified voltage; a third multiplying means for multiplying said electrical signals of said humidity and temperature sensors together and for also multiplying the result by a third specified voltage; a constant generating means for generating a fourth specified voltage, and an adding means for adding together said electrical signals of said first, second and third multiplying means and said constant generating means; wherein an output from said adding means is delivered as an enthalpy output.

2. An enthalpy output device as set forth in claim 1, wherein if said relative humidity is $\psi$ and said dry bulb temperature is t, then said first, second and third multiplying means, and said constant generating means, and said adding means together calculate a value equal to:

$$7.616 \times 10^{-3} \psi t + 0.2301 t - 0.06704 \psi + 0.1634.$$

3. An enthalpy output device comprising: a humidity sensor for converting a relative humidity into an electrical signal; a temperature sensor for converting a dry bulb temperature into an electrical signal; a first adding means for adding a first specified voltage to said electrical signal of said humidity sensor; a second adding means for adding a second specified voltage to said electrical signal of said temperature sensor; a multiplying means for multiplying said electrical signals of said first and second adding means together and also for multiplying the result by a third specified voltage; a constant generating means for generating a fourth specified voltage, and a third adding means for adding together said electrical signals of said multiplying means and said constant generating means, wherein an output from said third adding means is delivered as an enthalpy output.

4. An enthalpy output device as set forth in claim 3, wherein, if said relative humidity is $\psi$ and said dry bulb temperature is t, then said first, second and third adding means, and said constant generating means, and said multiplying means together calculate a value equal to:

$$a\left(t + \frac{c}{a}\right)\left(\psi + \frac{b}{a}\right) - \frac{bc}{a} + d$$

wherein:
a = 7.616 × 10$^{-3}$
b = 0.2301
c = 0.06704
d = 0.1634.

* * * * *